United States Patent [19]

Ichijima et al.

[11] 4,301,235
[45] Nov. 17, 1981

[54] PROCESS AND MATERIAL FOR FORMING COLOR PHOTOGRAPHIC IMAGE

[75] Inventors: Seiji Ichijima; Nobuo Furutachi, both of Minami-ashigara, Japan

[73] Assignee: Fuji Photo Film Co., Ltd., Minami-ashigara, Japan

[21] Appl. No.: 184,454

[22] Filed: Sep. 5, 1980

[30] Foreign Application Priority Data

Sep. 5, 1979 [JP] Japan .................. 54/114004

[51] Int. Cl.³ .............................. G03C 7/00
[52] U.S. Cl. .................. 430/387; 430/505; 430/555; 430/558
[58] Field of Search ........... 430/557, 558, 387, 505, 430/555

[56] References Cited

U.S. PATENT DOCUMENTS

| | | | |
|---|---|---|---|
| 3,990,899 | 11/1976 | Shiba et al. | 430/387 |
| 4,049,458 | 9/1977 | Boie et al. | 430/557 |
| 4,076,533 | 2/1978 | Ota et al. | 430/558 |
| 4,133,686 | 1/1979 | Ichijima et al. | 430/557 |

FOREIGN PATENT DOCUMENTS 2536191 3/1976 Fed. Rep. of Germany ...... 430/555

Primary Examiner—J. Travis Brown
Attorney, Agent, or Firm—Sughrue, Mion, Zinn, Macpeak and Seas

[57] ABSTRACT

A process for forming a color photographic image is described comprising processing a silver halide color phototgraphic light-sensitive material in the presence of a 5-pyrazolone magenta coupler represented by the formula (I)

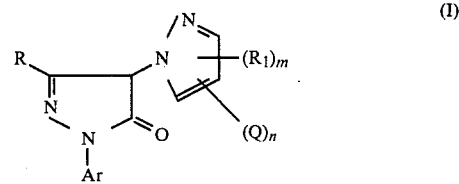

wherein R represents an acylamino group, an anilino group or a ureido group; $R_1$ represents a nitro group, a nitroso group, an amino group, an acylamino group, a sulfonamido group, a urethane group, a diacylamino group or a ureido group; Q represents hydrogen, a halogen atom, a substituted or unsubstituted alkyl group, an alkenyl group, a cycloalkyl group, an aralkyl group, an alkoxy group, an aryloxy group, a carboxy group, a substituted or unsubstituted aryl group, a substituted or unsubstituted heterocyclic group, a thiourethane group, a thioureido group, an acylhydrazino group, an alkylamino group, a dialkylamino group, an anilino group, an alkylthio group, a mercapto group, an arylthio group, an alkylsulfinyl group, an alkylsulfonyl group, an arylsulfinyl group, an arylsulfonyl group, a sulfamoyl group, a sulfo group, a thiocyano group, a hydroxy group, an aminocarbonyloxy group, an acyloxy group, a sulfonyloxy group, an alkylcarbonyl group, an arylcarbonyl group, an alkoxycarbonyl group, an aryloxycarbonyl group, a carbamoyl group, an aralkyloxycarbonyl group, a cyano group; Ar represents a phenyl group which may be substituted with one or more halogen atoms, alkyl groups, alkoxy groups or cyano groups; m represents an integer; n represents 0, 1 or 2; and m and n must satisfy the following relation, $1 \leq m+n \leq 3$.

The 2-equivalent magenta coupler represented by the formula (I) is stable to the attack of chemicals and capable of forming a magenta dye in high yield without forming undesired fog or stain.

26 Claims, No Drawings

PROCESS AND MATERIAL FOR FORMING COLOR PHOTOGRAPHIC IMAGE

BACKGROUND OF THE INVENTION

1. Field of the Invention

This invention relates to a color image forming process and a silver halide photographic light-sensitive material utilizing a novel two-equivalent magenta-color-forming coupler (also referred to herein simply as the "magenta coupler").

2. Description of the Prior Art

It is known that, upon color development of a silver halide color photographic material, an oxidized aromatic primary amine color developing agent reacts with a coupler to form an indophenol, indoaniline, indamine, azomethine, phenoxazine, phenazine or like dye, thereby forming color image. In such a system, color reproduction is usually based on subtractive color photography, and silver halide emulsions selectively sensitive to blue, green and red light, respectively, and yellow, magenta and cyan color image-forming compounds which are in a complementary color relation to the sensitivity of the respective emulsions are employed. For example, acylacetanilide or dibenzoylmethane couplers are generally used for the formation of a yellow color image; pyrazoline, pyrazolobenzimidazole, cyanoacetophenone and indazolone couplers are generally used for the formation of magenta color images, and phenolic couplers (e.g., phenols and naphthols) are generally used for the formation of cyan color images.

In one of the most preferred embodiments of color photographic light-sensitive materials, dye image-forming couplers are added to silver halide emulsions. Couplers added to emulsions must be rendered non-diffusible (or diffusion-resistant) in a binder matrix of the emulsions.

Most conventional color-image-forming couplers are 4-equivalent couplers. That is, the development of 4 mols of silver halide as an oxidizing agent is theoretically necessary to form 1 mol of dye through the coupling reaction. On the other hand, 2-equivalent couplers are also known, having an active methylene group substituted with a group (often referred to as a "coupling-off" group) eliminatable upon oxidative coupling of the coupler with an oxidation product of an aromatic primary amine developing agent. Such 2-equivalent require the development of only 2 mols of silver halide to form 1 mol of dye. Since 2-equivalent couplers require only one-half the silver halide as compared with conventional 4-equivalent couplers to form a dye, their use enables rapid processing of light-sensitive layers, improvement of the photographic properties due to a reduction in film thickness, and results is economic advantages.

Several approaches have thus far been suggested to produce 2-equivalent 5-pyrazolone couplers (primarily for use as magenta-forming couplers). For example, the substitution of the 4-position of a pyrazolone with a thiocyano group is described in U.S. Pat. Nos. 3,214,437 and 3,253,924, with an acyloxy group is described in U.S. Pat. No. 3,311,476, with an aryloxy group is described in U.S. Pat. No. 3,419,391, with a 2-triazolyl group is described in U.S. Pat. No. 3,617,291, and with a halogen atom is described in U.S. Pat. No. 3,522,052.

However, in using these 4-position substituted pyrazolone couplers, there are disadvantages, e.g.: serious color fog may result; the reactivity of the couplers may be unsuitable; the couplers may be chemically so unstable that they are converted to materials incapable of color formation with the lapse of time; or synthesis of the couplers is often difficult.

Also, it has hitherto been known to substitute the 4-position of a 5-pyrazolone with an alkylthio group, an arylthio group or a heterocyclic ring thio group, as described in U.S. Pat. No. 3,227,554. However, with many of these known thio-substituted pyrazolone compounds, the reactivity with the oxidation product of an aromatic primary amino color developing agent is unsuitable and, further, they are difficult to employ in ordinary color light-sensitive materials due to the strong photographic action of the mercapto compound produced as a result of the coupling reaction. In addition, the chemical stability of these couplers is not generally satisfactory.

Recently, 2-equivalent 5-pyrazolone magenta couplers having a heterocyclic substituent at the 4-position thereof have been disclosed in some patents. For example, an imidazolyl group and a derivative thereof, a 1,2,4-triazolyl group and a derivative thereof, and a 1,2,3-triazolyl group and a derivative thereof are described in German Patent Application (OLS) 2,536,191, and a 1,2,4-triazolyl group and a derivative thereof are described in German Patent Application (OLS) 2,651,363.

The compounds described in the above-mentioned patents show good color forming properties, and thus satisfy one of the characteristics required of 2-equivalent magenta couplers. However, those couplers having an imidazolyl group or a 1,2,4-triazolyl group still also have some disadvantages. For example, their use is accompanied by a decrease in the sensitivity of the silver halide due to interaction with the silver halide (for example, by adsorption onto the light-sensitive center of silver halide, etc.).

SUMMARY OF THE INVENTION

Therefore, an object of the present invention is to provide a novel 2-equivalent magenta coupler in which the coupling position (i.e., the 4-position) is substituted with a group eliminatable upon coupling with an oxidation product of an aromatic primary amine developing agent.

Another object of the present invention is to provide a color photographic light-sensitive material having high sensitivity using a novel 2-equivalent magenta coupler.

A further object of the present invention is to provide a color photographic light-sensitive material having a silver halide emulsion layer containing a novel magenta color image-forming coupler.

A still further object of the present invention is to provide a process for reducing the amount of silver halide in a photographic emulsion layer by using a novel 2-equivalent magenta color-image-forming coupler therein, thus allowing for thinner emulsion layers and improving the sharpness of color images obtained.

A still further object of the present invention is to provide a color photograph having a fast color image by using a novel magenta color image-forming coupler.

An even further object of the present invention is to provide a novel 2-equivalent magenta coupler which can be synthesized with ease and in high yield.

It is also an object of the present invention to provide a 2-equivalent magenta coupler showing an improved degree of conversion to dye, having improved resistance to a reduction in coloration due to the attack of chemicals, and having excellent coloration reactivity.

It is also an object of the present invention to provide a novel 2-equivalent magenta coupler having suitable reactivity and capable of forming a dye in high yield without forming undesired fog or stain.

These and other objects of the present invention will become apparent from the following detailed description and examples.

These objects of the invention are attained by a process using a novel photographic coupler represented by the formula (I) described below and, particularly, by using a color photographic light-sensitive material comprising a support having thereon at least one silver halide emulsion layer with at least one of the silver halide emulsion layers containing a novel 2-equivalent magenta coupler represented by the formula (I) described below.

The couplers according to the invention are represented by the formula (I)

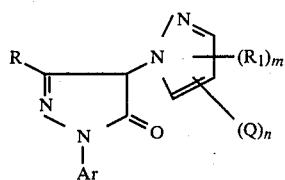

wherein R represents an acylamino group, an anilino group or a ureido group; $R_1$ represents a nitro group, a nitroso group, an amino group, an acylamino group, a sulfonamido group, a urethane group, a diacylamino group or a ureido group; Q represents hydrogen, a halogen atom, a substituted or unsubstituted alkyl group, an alkenyl group, a cyclo-alkyl group, an aralkyl group, an alkoxy group, an aryloxy group, a carboxy group, a substituted or unsubstituted aryl group, a substituted or unsubstituted heterocyclic group, a thiourethane group, a thioureido group, an acylhydrazino group, an alkylamino group, a dialkylamino group, an anilino group, an alkylthio group, a mercapto group, an arylthio group, an alkylsulfinyl group, an alkylsulfonyl group, an arylsulfinyl group, an arylsulfonyl group, a sulfamoyl group, a sulfo group, a thiocyano group, a hydroxy group, an aminocarbonyloxy group, an acyloxy group, a sulfonyloxy group, an alkylcarbonyl group, an arylcarbonyl group, an alkoxycarbonyl group, an aryloxycarbonyl group, a carbamoyl group, an aralkyloxycarbonyl group, a cyano group; Ar represents a phenyl group which may be substituted with one or more halogen atoms, alkyl groups, alkoxy groups or cyano groups; m represents an integer; m represents 0, 1 or 2; and m and n must satisfy the following relation, $1 \leq m + n \leq 3$.

DETAILED DESCRIPTION OF THE INVENTION

Examples of the acylamino groups for R include an aliphatic acylamino group having 2 to 30 carbon atoms or an aromatic acylamino group having 6 to 32 carbon atoms which may be substituted with a halogen atom, an acylamino group, an alkoxy group, an aryloxy group, an aryl group, a sulfonamido group, a sulfamoyl group, an alkoxycarbonyl group, an imido group, a cyano group, a carboxy group, an alkylcarbonyl group, an aryloxycarbonyl group, a sulfo group, an acyloxy group, a carbamoyl group, a ureido group, a urethane group, a heterocyclic group, an alkylsulfonyl group, an arylthio group, an alkylthio group, an anilino group, a hydroxy group, an arylsulfonyl group, etc., such as, for example, an acetamido group, a benzamido group, a 3-[α-(2,4-di-tert-amylphenoxy)butyramido]benzamido group, a 3-[α-(2,4-di-tert-amylphenoxy)acetamido]benzamido group, a 3-[α-(3-pentadecylphenoxy)-butyramido]benzamido group, an α-(2,4-di-tert-amylphenoxy)butyramido group an α-(3-penta-decylphenoxy)butyramido group, etc.

The anilino groups for R may be substituted with a straight or branched chain alkyl, alkenyl, aralkyl or aryl group, and the same groups as described above for the acylamino group, and have 6 to 32 total carbon atoms (inclusive of the anilino moiety). Representative examples include an unsubstituted anilino group, a 2-chloroanilino group, a 2,4-dichloranilino group, a 2-chloro-5-tetradecanamidoanilino group, a 2-chloro-5-(2-octadecenylsuccinimido)-anilino group, a 2-chloro-5-[α-(3-tert-butyl-4-hydroxy)-tetradecanamido]anilino group, a 2-chloro-5-tetradecyloxycarbonylanilino group, a 2-chloro-5-(N-tetradecylsulfamoyl)anilino group, a 2,4-dichloro-5-tetradecyloxyanilino group, etc.

The ureido groups for R may be substituted by the same groups as above-described acylamino group. Representative examples include a 3-[(2,4-di-tert-amylphenoxy)-acetamido]phenylureido group, a phenylureido group, a methylureido group, an octadecylureido group, a 3-tetradecanamidophenylureido group, etc.

Of the groups represented by $R_1$, the acylamino group, the sulfonamido group, the urethane group, the diacylamino group and the ureido group can be represented by the formulae (II), (III), (IV), (V) and (VI), respectively.

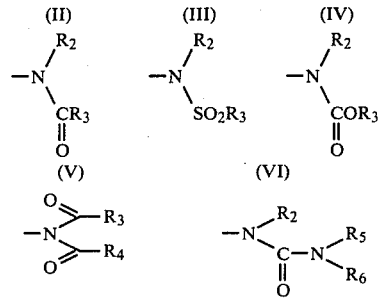

Of the formulae (II) to (VI) described above, the formulae (II) and (III) are particularly preferred. In the above formulae, $R_2$, $R_5$ and $R_6$ each represents hydrogen, a straight chain or branched chain alkyl group, an alkenyl group, a cycloalkyl group, an aralkyl group, an aryl group or a heterocyclic group; and $R_3$ and $R_4$ each represents a straight chain or branched chain alkyl group, an alkenyl group, a cycloalkyl group, an aralkyl group, an aryl group or a heterocyclic group. Alternatively $R_2$ and $R_3$, $R_3$ and $R_4$, $R_2$ and $R_5$, and $R_5$ and $R_6$ together, respectively, can form a 5-membered, 6-membered or 7-membered nitrogen containing heterocyclic ring.

The alkyl group, the alkenyl group, the cycloalkyl group and the aralkyl group represented by $R_2$, $R_3$, $R_4$, R5 and R6 in the general formulae (II), (III), (IV), (V) and (VI) described above generally may contain from 1 to 36 carbon atoms, and preferably contain from 1 to 22 carbon atoms. These groups can have one or more substituents. Examples of the substituents include a halogen atom, a nitro group, a cyano group, a thiocyano group, an aryl group, an alkoxy group, an aryloxy group, a carboxy group, a sulfoxy group, an alkylcarbonyl group, an arylcarbonyl group, an alkoxycarbonyl group, an aryloxycarbonyl group, a sulfo group, an acyloxy group, a sulfomoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, a mercapto group, etc.

Furthermore, when any of $R_2$, $R_3$, $R_4$, $R_5$ and $R_6$ represents an aryl group (for example, a phenyl group, an α-naphthyl group, a β-naphthyl group, etc.) or a heterocyclic group (for example, an oxazolyl group, a thiazolyl group, a furyl group, an α-pyridyl group, etc.) these groups can have one or more substituents, for example, an alkenyl group, a cycloalkyl group, an aralkyl group, etc., as well as the substituents as described above for the alkyl alkenyl, cycloalkyl, and analkyl groups.

The pyrazole ring attached to the 4-position of the 5-pyrazolone ring in the coupler according to the formula (I) may be substituted with two or threee groups represented by $R_1$. In such a case these groups may be the same or different.

Ar in the formula (I) can represents a phenyl group which may be substituted with one or more halogen atoms (for example, fluorine atoms, chlorine atoms, bromine atoms), straight chain or branched chain alkyl groups having from 1 to 35 carbon atoms, and preferably from 1 to 22 carbon atoms, alkoxy groups containing a straight chain or branched chain alkyl group having from 1 to 35 carbon atoms, and preferably 1 to 22 carbon atoms or cyano groups.

Preferred examples of the substituted pyrazolyl group attached to the 4-position of the 5-pyrazolone ring in couplers according to the formula (I) are illustrated below.

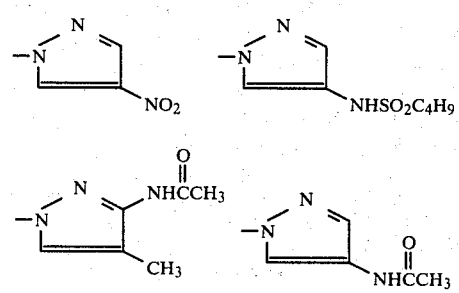

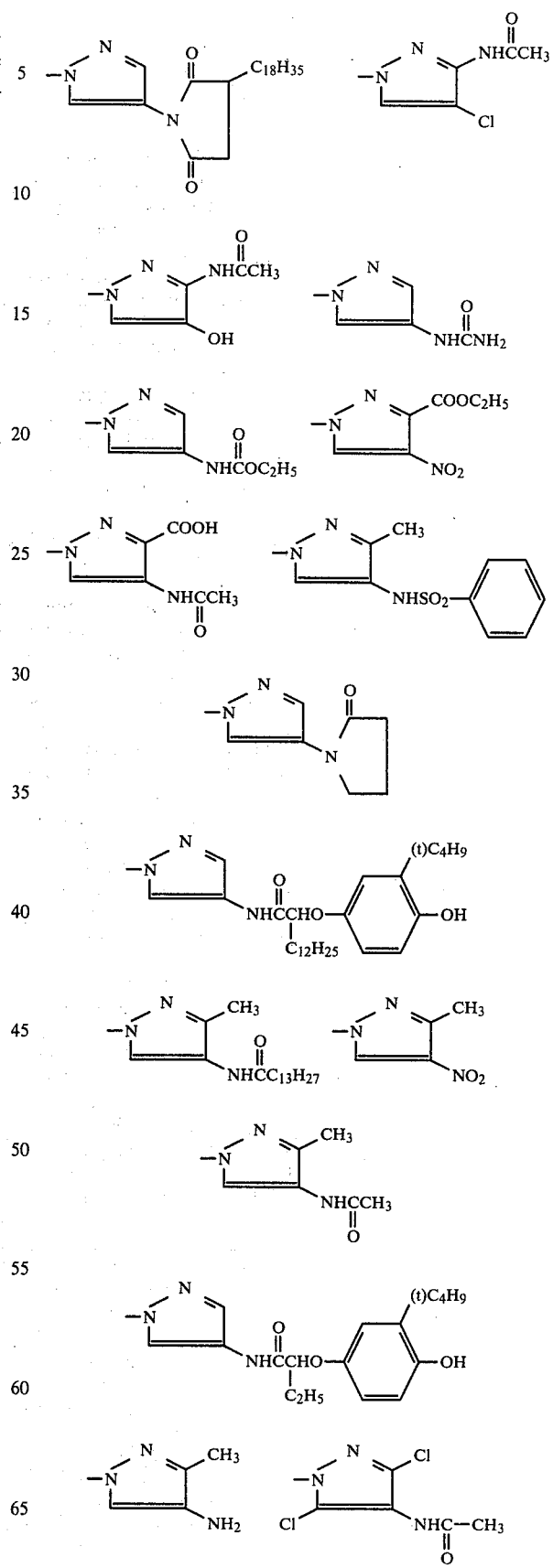

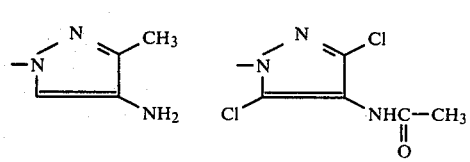

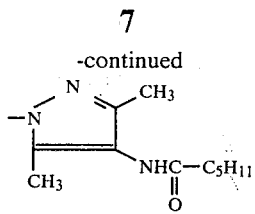

The coupler of the present invention represented by the general formula (I) can be a symmetrical or an asymmetrical complex coupler formed by linking two coupler moieties to each other by the substituents of R and Ar or through an R or Ar divalent group.

The magenta couplers used in the present invention provide various properties depending upon the particular R, $R_1$, the substituents on the pyrazole ring other than $R_1$, and the Ar substituents, and can be emloyed for various photographic purposes. When at least one of Ar and R contains a hydrophobic residue having 8 or more carbon atoms, the coupler is rendered nondiffusible when associated with a hydrophilic colloidal layer of a light-sensitive material. Such a coupler can be usefully incorporated in a silver halide emulsion layer.

Couplers having a diffusion-resistant hydrophobic residue in the substituents on the pyrazole ring and containing a water-solubilizing group such as a sulfo group or a carboxy group in at least one of Ar and R provide a diffusible dye through an oxidation coupling reaction with an aromatic primary amine developing agent, although the couplers themselves are non-diffusible. Such couplers which are capable of providing diffusible dyes are useful for diffusion transfer color photography.

The process of forming dye images through oxidative coupling reaction with an aromatic primary amine developing agent can be classified into two types, depending on the manner of addition of the couplers. One type is a so-called incorporated-coupler process wherein the couplers are incorporated in an emulsion layer during the production of a light-sensitive material. The other type is a so-called unincorporated-coupler process wherein the couplers are dissolved in a developer and are supplied, upon development, through diffusion into an emulsion layer.

Couplers for use in an incorporated-coupler type multilayer system must be immobilized in an emulsion layer, i.e., must be made diffusion-resistant. Otherwise, couplers would migrate through the light-sensitive material and form color in an unintended emulsion layer, having a different color sensitivity, thus seriously degrading the color reproducibility of the light-sensitive material. In order to render the couplers diffusion-resistant, a group having a hydrophobic residue containing from 8 to 32 carbon atoms is introduced into the couplers molecule. Such a residue is called a ballasting group. This ballasting group can be connected to the coupler skeletal structure directly or through an imino bond, an ether bond, a carbonamido bond, a sulfonamido bond, a ureido bond, an ester bond, an imido bond, carbamoyl bond, a sulfamoyl bond, or the like.

Several specific examples of such ballasting group are described in the specific examples of the couplers of the invention.

Typical examples of the ballasting groups include, e.g., an alkyl group, an alkoxyalkyl group, an alkenyl group, an aryl group substituted by an alkyl group, an aryl group substituted by an alkoxy group, a terphenyl group, and the like. These ballasting groups may be substituted by, for example, a halogen atom (e.g., fluorine, chlorine, etc.), a nitro group, a cyano group, an alkoxycarbonyl group, an amido group, a carbamoyl group, a sulfonamido group, etc. Specific examples of the ballasting group include an n-octyl group, a 2-ethylhexyl group, a tert-octyl group, an n-nonyl group, an n-decyl group, an n-dodecyl group, a 1,1-dimethyldecyl group, a 2,2-dimethyldecyl group, an n-octadecyl group, a 2-(n-hexyl)decyl group, an n-octadecyl group, a 9,10-dichlorooctadecyl group, a heptyloxyethyl group, an oleyl group, a 2,4-di-tert-butylphenyl group, a 2,4-di-tert-amylphenyl group, a 2,4-di-tert-amyl-6-chlorophenyl group, a 3-n-pentadecylphenyl group, a 2-dodecyloxyphenyl group, a 3-heptadecyloxyphenyl group, an o-terphenyl group, a perfluoroheptyl group, etc.

The couplers according to the present invention can be obtained, in general, by the reaction of a magenta coupler having a halogen atom in the coupling position with a pyrazole compound according to the following reaction scheme:

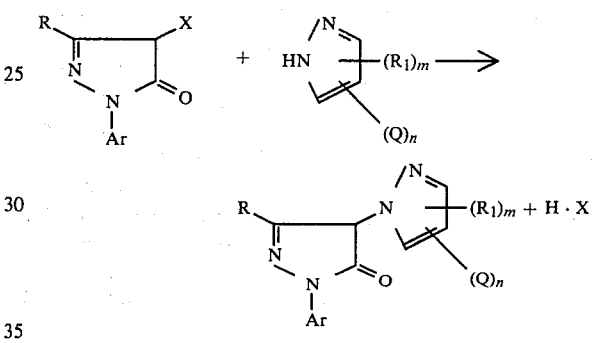

wherein R, $R_1$, Q, Ar, m and n each has the same meaning as defined above, and X represents a halogen atom (for example, a chlorine atom, a bromine atom, etc.) substituted in the coupling position of the magenta coupler. The 4-halogeno-5-pyrazolones can be synthesized from a 5-pyrazolone ring according to the process described, for example, in U.s. Pat. Nos. 3,006,759 and 3,522,051.

Also, when an electron-donating group such as an anilino group is substituted in the 3-position of a 5-pyrazolone, the mono-halo-substituted couplers can be synthesized with each by converting the coupler to a 3-N-alkoxycarbonyl-anilino-5-pyrazolone derivative or a 3-N-acetyl-anilino-5-pyrazolone derivative, and halogenating the resulting 3-substituted coupler. For example, a bromination reaction can be accomplished in the presence of 2 to 20 ml of a solvent such as chloroform, dichloromethane, acetic acid, etc., per 1 g of 5-pyrazoline and in the presence or absence of bases such as sodium acetate, triethylamine, etc., under a temperature of $-5°$ to 20° C. Halogenation of the coupler is illustrated in the Synthesis Examples described hereinafter.

The reaction between the thus produced 4-halogeno-5-pyrazolone and the pyrazole compound can be effected at a temperature of from about 0° to 200° C. in various solvents, or in the absence of a solvent by melting the reactants. Preferred temperatures range from about 20° C. to 150° C. and, where the reactants are reacted by non-solvent melting methods, the temperature needs to be no higher than the melting point as long as both reactants are soluble at that temperature. Illustrative preferred solvents include alcoholic solvents (e.g., methanol, ethanol, propanol, etc.), aromatic solvents (e.g., benzene, toluene, xylene, etc.), aprotic polar solvents (e.g., dimethylformamide, hexamethylphosphotriamide, etc.), and the like.

Since the pyrazole compounds present in an excess amount can be used as a dehydrohalogenating agent, it is not necessary to use a base therefor. However, a base such as 1,8-Diazabicyclo(5,4,0)-7-undecene-2,6-lutidine, sodium acetate, etc. can be used if desired.

The pyrazole compounds can be synthesized by reference to the methods described, for example, in The Journal of Organic Chemistry, Vol. 38, page 1777 (1973), ibid., Vol. 36, page 3081 (1971), ibid., Vol. 43, page 1367 (1978), Journal of the American Chemical Society, Vol. 78, page 2148 (1956), Journal of the Chemical Society, page 3259 (1958), etc.

The coupler of the present invention can advantageously be mixed with a solvent dispersion by dissolving the coupler in a water-immiscible organic solvent having a melting point of about 170° C. or higher, a low-boiling organic solvent or a water soluble organic solvent, or in a high-boiling, water-immiscible organic solvent and/or a low boiling and/or water-soluble organic solvent.

Any of the high-boiling, water-immiscible organic solvents described in U.S. Pat. No. 2,322,027 can be used as a solvent. Preferred solvents include di-n-butyl phthalate, benzyl phthalate, triphenyl phosphate, tri-o-cresyl phosphate, diphenyl mono-p-t-butylphenyl phosphate, monophenyl di-o-chlorophenyl phosphate, dioctyl phthalate, dibutyl sebacate, acetyl tributyl citrate, tri-t-octyl trimellitate, n-nonylphenol, dioctylbutyl phosphate, N,N- diethyllaurylamide, 3-pentadecylphenyl ethyl ether, 2,5-disec-amyl-phenyl butyl ether, and so forth.

Low-boiling organic solvents (having a boiling point of not higher than about 170° C.) or water-soluble organic solvents usable together with or in place of the high-boiling solvents are described in U.S. Pat. Nos. 2,801,171, 2,801,170, 2,949,360, etc. Examples of these organic solvents include the following solvents:

(1) Low-boiling, substantially water-insoluble organic solvents such as methyl acetate, ethyl acetate, propyl acetate, butyl acetate, isopropyl acetate, ethyl propionate, sec-butyl alcohol, ethyl formate, butyl formate, nitromethane, nitroethane, carbon tetrachloride, chloroform, and so forth.

(2) Water-soluble organic solvents such as methyl isobutyl ketone, β-ethoxyethyl acetate, tetrahydrofurfuryl adipate, Carbitol acetate (diethyleneglycol monoacetate), methoxytriglycol acetate, methyl Cellosolve acetate, acetylacetone, diacetonealcohol, butyl Carbitol, butyl Cellosolve, methyl Carbitol, methyl ethyl ketone, methanol, ethanol, acetonitrile, dimethylformamide, dioxane, and so forth.

The water content present in the solvent solution should be sufficiently low so that the solubility of the coupler is not affected.

After production, the low-boiling or water-soluble solvent can be removed from a cooled noodle-like dispersion by air-drying or continuously washing with water as described in, e.g., U.S. Pat. No. 2,801,171.

A homogenizer for emulsification, a colloid mill, an ultrasonic wave emulsifying apparatus, etc., are useful for dispersing oil-soluble couplers. Diffusion-resistant couplers having a carboxylic acid group or a sulfonic acid group in their molecule together with a ballasting group are soluble in a neutral or a weakly alkaline aqueous solution. These couplers can be incorporated into a photographic emulsion by adding an aqueous solution thereof to the photographic emulsion. These couplers are believed to be rendered diffusion-resistant through formation of micelles in a hydrophilic high molecular weight material.

Specific examples of the couplers according to the present invention are illustrated below, but the magenta couplers which can be used in the present invention are not to be construed as being limited to these examples.

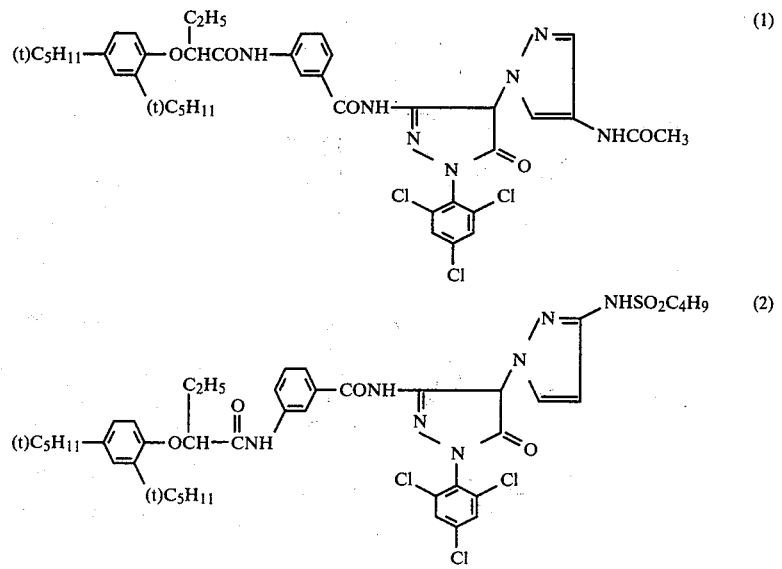

-continued
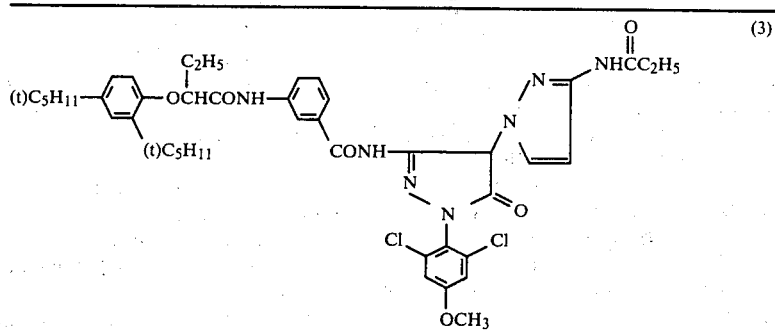 (3)
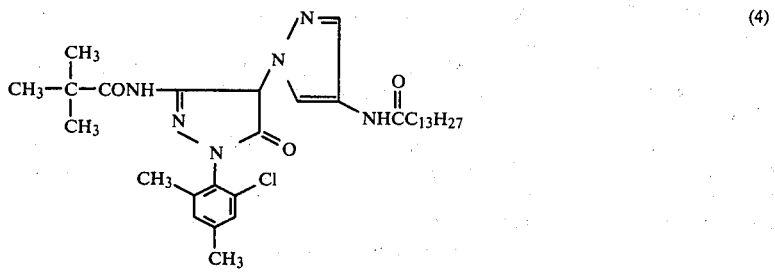 (4)
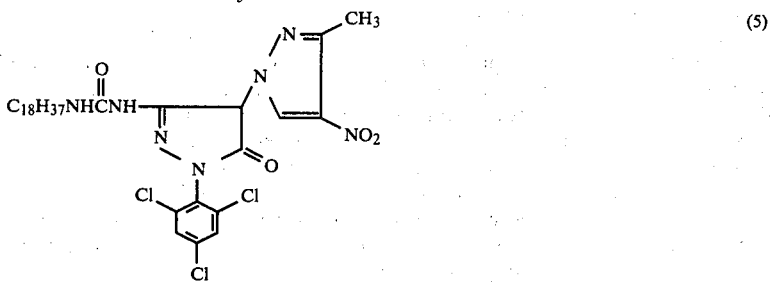 (5)
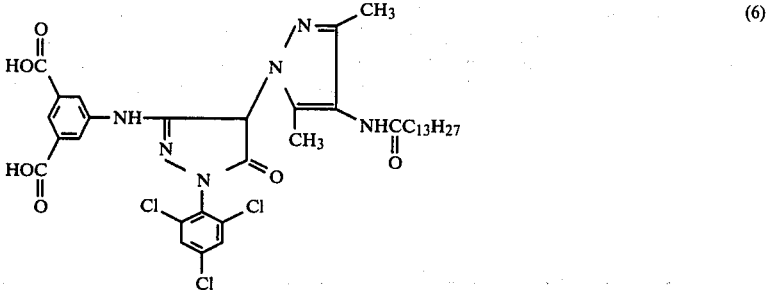 (6)
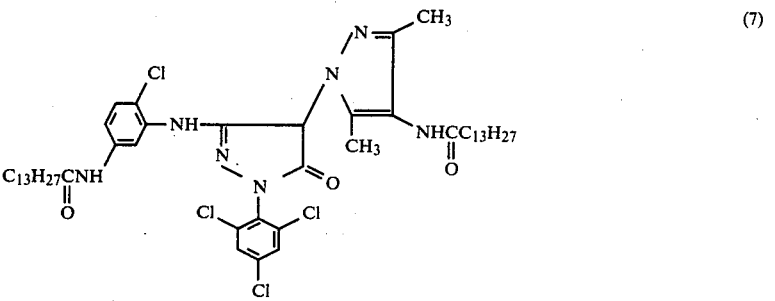 (7)
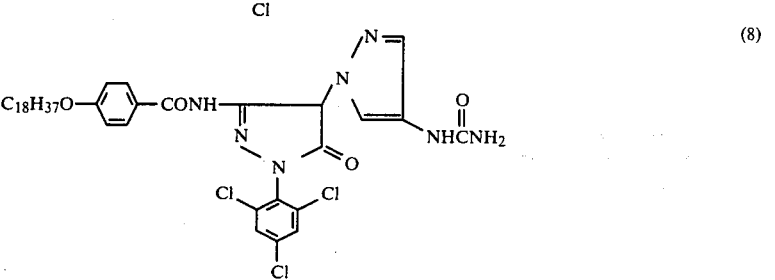 (8)

-continued
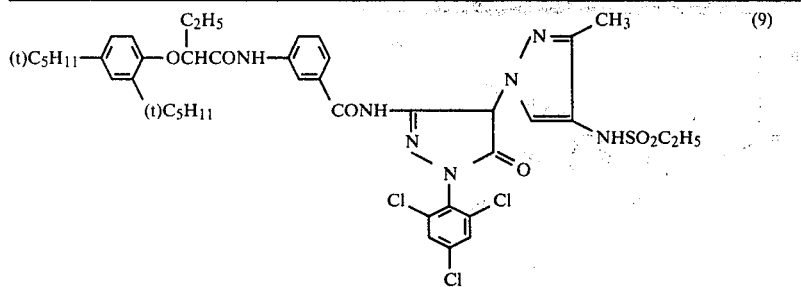 (9)
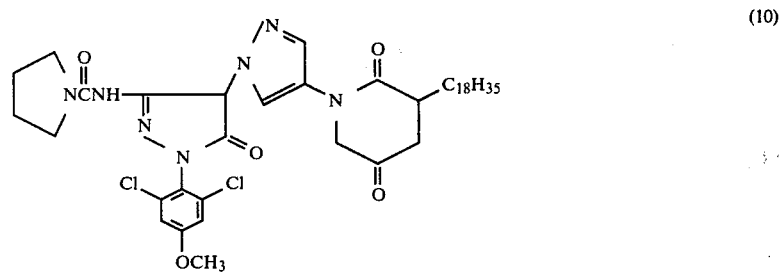 (10)
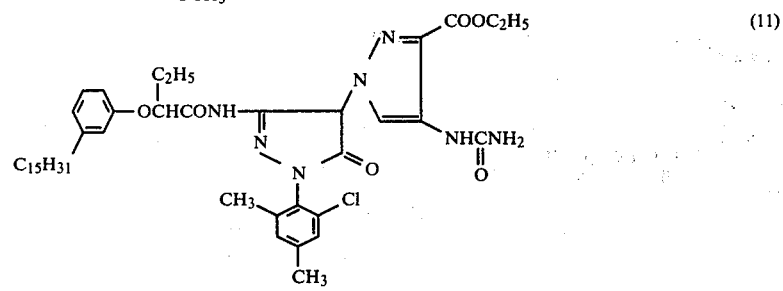 (11)
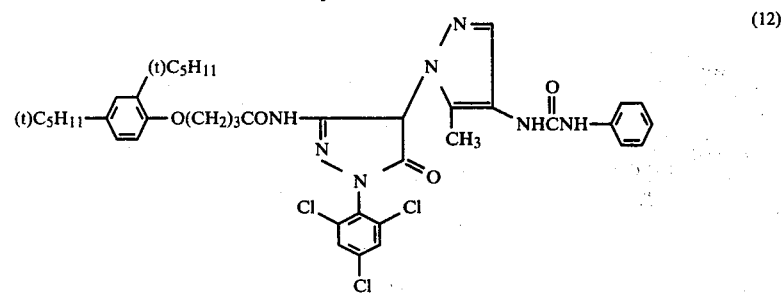 (12)
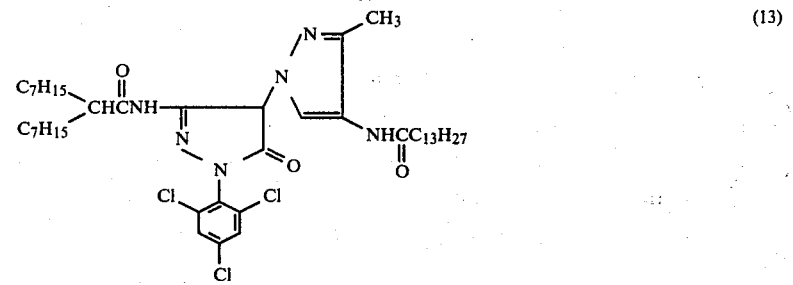 (13)
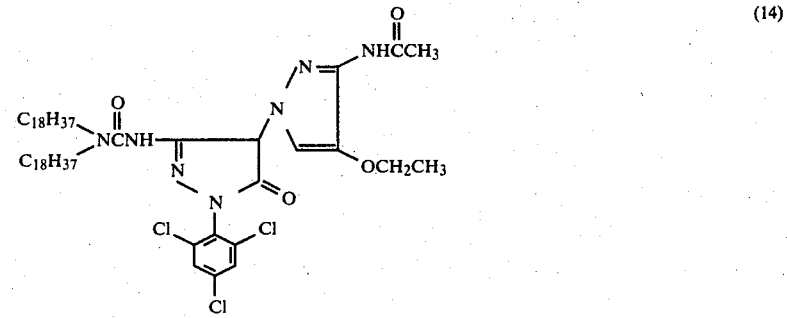 (14)

-continued
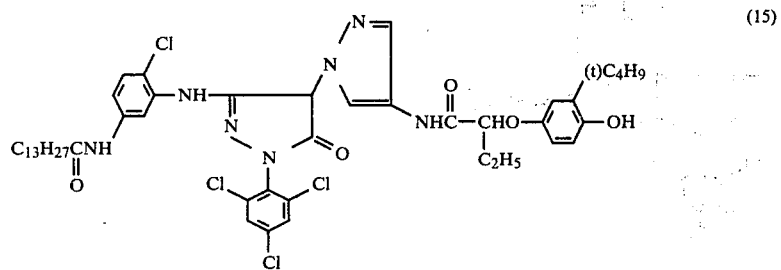
(15)
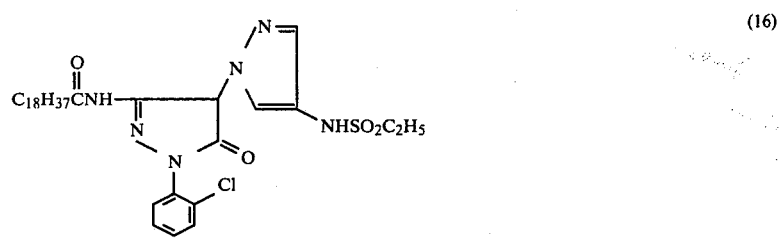
(16)
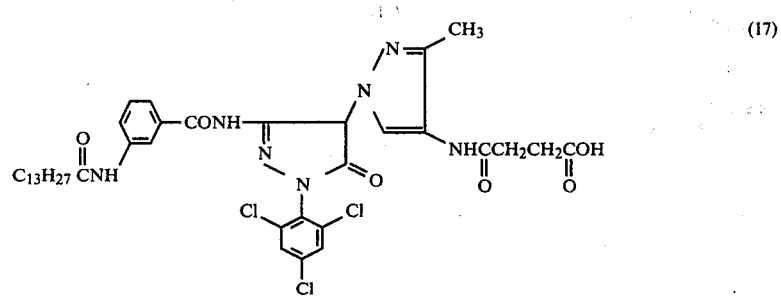
(17)
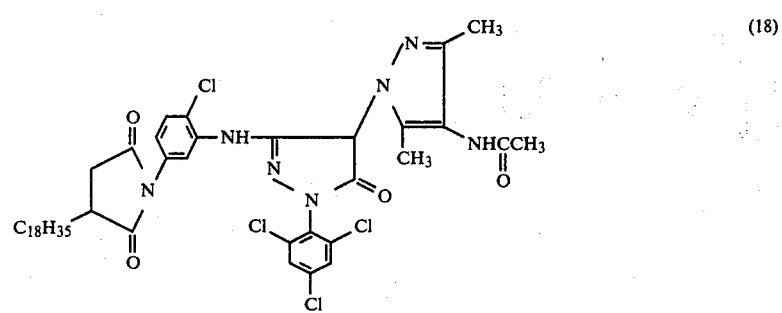
(18)
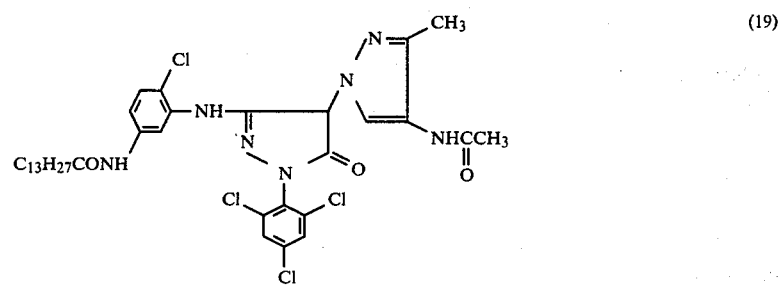
(19)
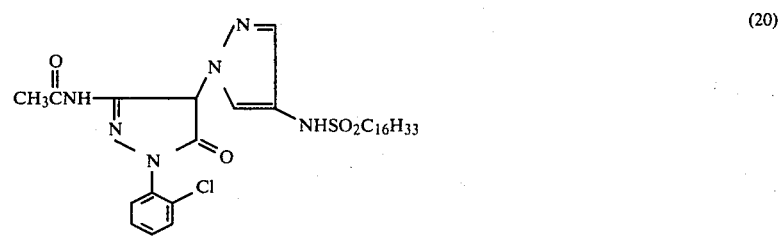
(20)

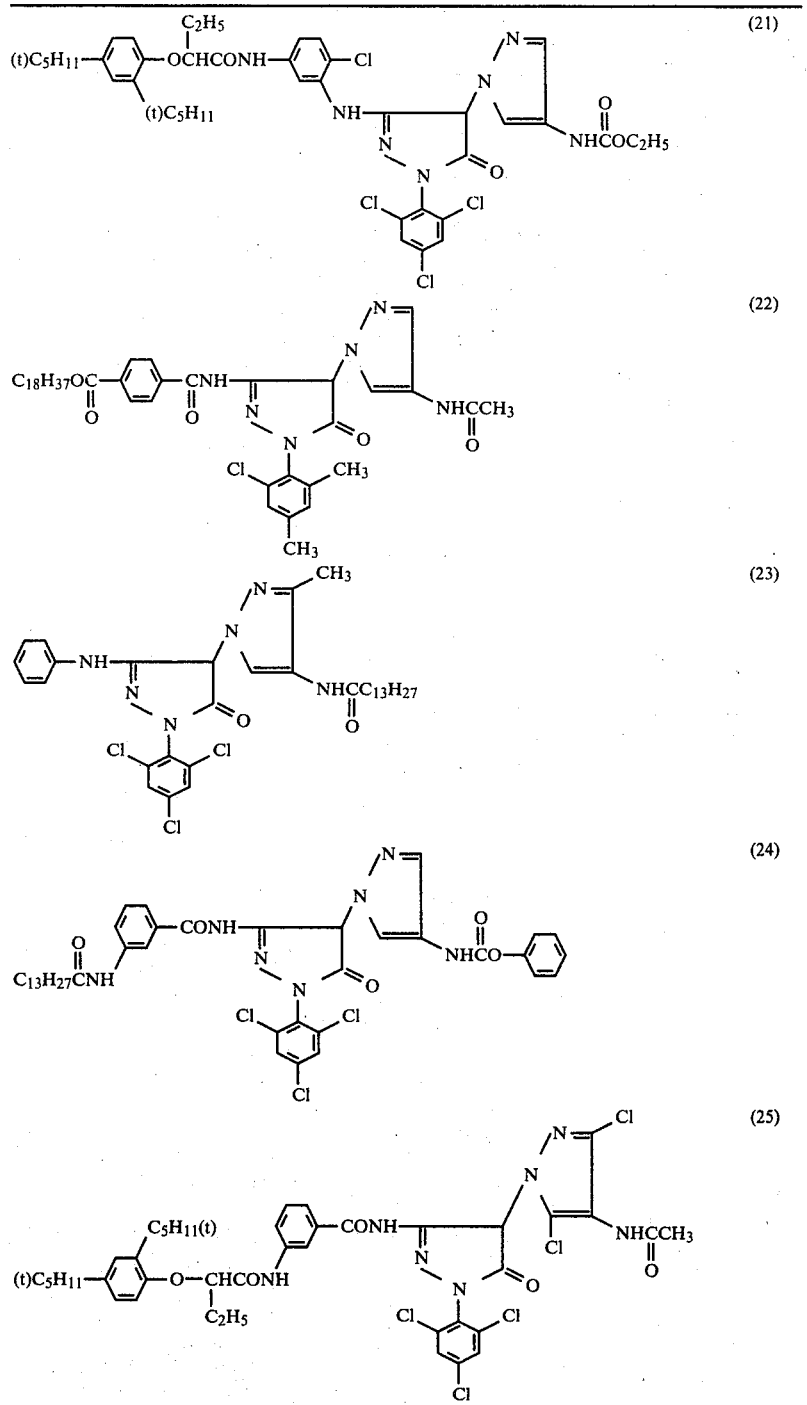

Typical examples of the synthesis of the photographic couplers of the present invention are described below.

SYNTHESIS EXAMPLE 1

Synthesis of 4-(4-Acetamido-1-pyrazolyl)-3-{3-[2-(2,4-di-tert-amylphenoxy)butyramido]benzamido}-1-(2,4,6-trichlorophenyl)-5-oxo-2-pyrazoline [Coupler (1)]:

17.8 g of 1-(2,4,6-trichlorophenyl)-3-{3-[2-(2,4-di-tert-amylphenoxy)butyramido]benzamido}-4-bromo-5-oxo-2-pyrazoline and 10 g of 4-acetamidopyrazole were well mixed in a mortar and heated at 100° C. for 2 hours. To the reaction mixture, 200 cc of ethyl acetate was added and the mixture was washed several times with water. The ethyl acetate layer was dried with anhydrous sodium sulfate and concentrated. Upon crystallization of the residue from a solvent mixture of acetonitrile and ethyl acetate, 12.1 g of Coupler (1) was obtained. The melting point of the coupler was 135° to 141° C.

SYNTHESIS EXAMPLE 2

Synthesis of 3-{3-[2-(2,4-Di-tert-amylphenoxy)-butyramido]-benzamido}-4-(4-butanesulfonamido-1-pyrazolyl)-1-(2,4,6-trichlorophenyl)-5-oxo-2-pyrazoline [Coupler (2)]:

The coupler was synthesized in the same manner as described in Synthesis Example 1 except using the equimolar amount of 4-butanesulfonamidopyrazole in place of 4-acetamido pyrazole. The desired coupler was obtained by crystallization from a solvent mixture of acetonitrile and benzene. The melting point of the coupler was 93° to 98° C.

SYNTHESIS EXAMPLE 3

Synthesis of 1-(2,4,6-Trichlorophenyl)-4-(3-methyl-4-nitro-1-pyrazolyl)-3-(3-octadecylureido)-2-pyrazolin-5-one [Coupler (5)]:

13 g of 4-bromo-1-(2,4,6-trichlorophenyl)-3-(3-octadecylureido)-2-pyrazolin-5-one and 10 g of 3-methyl-4-nitropyrazole were mixed at 90° C. for 2 hours. To the reaction mixture, 200 ml of ethyl acetate was added and the mixture was washed several times with water. The ethyl acetate layer was dried with anhydrous sodium sulfate and concentrated. The residual oil was dissolved in 50 ml of chloroform and purified with column chromatography using 500 g of silica gel (art 7734 manufactured by MERCK & Co.) wetted with chloroform as a bulking agent. Upon elution with a solvent mixture of chloroform and ethyl acetate (10:1), 10.9 g of an oily comprising the desired coupler was obtained.

IR (nujol) 1660, 1560, 1345 cm$^{-1}$

| Elemental Analysis for $C_{32}H_{46}N_7O_4Cl_3$ | | | |
|---|---|---|---|
| | C (%) | H (%) | N (%) |
| Calculated: | 54.97 | 6.63 | 14.03 |
| Found: | 54.72 | 6.66 | 14.25 |

SYNTHESIS EXAMPLE 4

Synthesis of 3-Anilino-1-(2,4,6-trichlorophenyl)-4-(3-methyl-4-tetradecanamido-1-pyrazolyl)-5-oxo-2-pyrazoline [Coupler (23)]:

Step 1: Synthesis of 3-Anilino-1-(2,4,6-trichlorophenyl)-4-(3-methyl-4-nitro-1-pyrazolyl)-5-oxo-2-pyrazoline 20 g of 4-bromo-1-(2,4,6-trichlorophenyl)-3-(anilino)-5-oxo-2-pyrazoline which was prepared by the method described in Japanese Patent Application (OPI) No. 91862/77 and 21 g of 3-methyl-4-nitropyrazole were mixed and heated at 100° C. for 7 hours. After cooling, 300 ml of a 10% methanol solution of potassium hydroxide was added to the reaction mixture, followed by stirring for 5 hours at room temperature. To the reaction mixture, 1 liter of ethyl acetate was added and the mixture was washed with 1 liter of 1 N hydrochloric acid then washed several times with water. The oil layer was separated and concentrated. Upon crystallization of the residue from 100 ml of acetonitrile, 17 g of the desired compound was obtained.

Step 2: Synthesis of 3-Anilino-1-(2,4,6-trichlorophenyl)-4-(4-amino-3-methyl-1-pyrazolyl)-5-oxo-2-pyrazoline 17 g of the 3-aniline-1-(2,4,6-trichlorophenyl)-4-(3-methyl-4-nitro-1-pyrazolyl)-5-oxo-2-pyrazoline obtained in Step 1 was suspended in 200 ml of ethanol. After adding a catalytic amount of palladium carbon to the mixture, the mixture was subjected to catalytic reduction in an autoclave of 50 atoms of hydrogen pressure at room temperature for 5 hours. The reaction mixture was filtered and the filtrate was concentrated. The residue was used in Step 3 without further purification.

Step 3: Synthesis of 3-Anilino-1-(2,4,6-trichlorphenyl)-4-(3-methyl-4-tetradecanamido-1-pyrazolyl)-5-oxo-2-pyrazoline [Coupler (23)]

The 4-(4-amino-3-methyl-1-pyrazolyl)-3-anilino-1-(2,4,6-trichlorophenyl)-5-oxo-2-pyrazoline obtained in Step 2 was suspended in 100 ml of acetonitrile and stirred with heating. To the solution, 9 g of tetradecanoylchloride was added and the mixture was refluxed for 2 hours. To the reaction mixture, 500 ml of ethyl acetate was added and the mixture was washed several times with water. The oil layer was dried with anhydrous sodium sulfate and concentrated. Upon crystallization of the residue from a solvent mixture of acetonitrile and benzene, 8 g of Coupler (23) was obtained. The melting point of the coupler was 123° to 131° C.

The couplers of the present invention are 2-equivalent couplers. That is, they require stoichiometrically only 2 equivalents of silver halide as an oxidizing agent to produce 1 molecule of dye.

In comparison with conventionally widely used 4-equivalent pyrazolone type couplers, the 2-equivalent couplers of the present invention require only about one-half the amount of silver halide. Thus the amount of silver halide incorporated in a light-sensitive material can be reduced to about one-half that amount required with 4-equivalent couplers. Therefore, not only is the production cost of light-sensitive materials reduced, but also light scattering is reduced as well, improving the sharpness of the images.

The magenta coupler of the present invention can be converted to an azomethine dye in a high yield through an oxidative coupling reaction wherein exposed silver halide acts as an oxidizing agent. With some conventionally used 4-equivalent couplers, a leuco dye which is an intermediate in dye formation undergoes side reactions, with an azine ring or the like being formed, resulting in a low conversion yield to the dye. On the other hand, the magenta couplers of the present invention can be converted to an azomethine dye in high yield, since such a reactive intermediate is not formed. As a result, the amount of the magenta-forming coupler used in the color light-sensitive material of the present invention can be reduced, which leads to a reduction in silver halide content and in the thickness of an emulsion layer and thus to a reduction of the production cost of the light-sensitive materials, an improvement in the sharpness and facilitating rapid development processing.

The magenta coupler of the present invention has such a strong coupling activity for an oxidized aromatic primary amine color developing agent that the oxidation product of the developing agent produced upon color development is rapidly removed, thus accelerating the development of the silver halide emulsion.

Suitable amounts of the magenta coupler of the present invention are from $2 \times 10^{-3}$ to $5 \times 10^{-1}$ mol, and preferably from $1 \times 10^{-2}$ to $5 \times 10^{-1}$ mol per mol of silver (in the form of photographic silver halide).

With the magenta coupler of the present invention, the process of forming a dye is completed in a color developing bath, which enables the materials to be processed with a bleach-fixing bath containing a weak oxidizing agent such as Fe (III) chelate of ethylenediaminetetraacetic acid (EDTA) or the like and a silver complex salt-forming agent or a ferric salt (e.g., ferric chloride) without using a bleaching bath containing a strong oxidizing agent such as potassium ferricyanide or potassium dichromate. This results in a shortening of the time required for the processing steps of color development and minimizes the problem of environmental pollution due to discharge of processing waste water.

The coupling position substituted magenta couplers of the present invention are less inactivated by the action of carbonyl compounds such as aldehydes or ketones. Conventionally used coupling position unsubstituted magenta couplers are often changed into compounds having a low color reaction activity, such as a methylol or methylenebis compounds, when contacted with formaldehyde or the like in the air especially in an emulsion layer, and thus fail to attain sufficient coloration through color development. The color light-sensitive material of the present invention has the advantage that it is affected to a much lesser extent by such chemicals.

The magenta coupler of the present invention, when it is used for ordinary color light-sensitive materials, as described in the Examples, has high stability over a long period of time, and undergoes only a slight reduction in coloring property when stored at a low temperature under high humidity as compared with the above-described known 2-equivalent couplers. The stability of a color light-sensitive material after production is one of the most important factors in evaluating the characteristics of light-sensitive materials. Also, colored images resulting from the magenta coupler of the present invention have markedly superior heat-fastness as compared with couplers which are not substituted in the coupling position. Even in comparison with the above-described known couplers with the same pyrazolone nucleus and having other substituents in the 4-position, the colored image formed from the magenta coupler of the present invention is found to exhibit greater heat resistance.

The couplers in accordance with the present invention can be employed in light-sensitive materials containing a reduced amount of silver halide, i.e, about several tenths to about 1/100 as much as the amount in ordinary color light-sensitive materials. For example, suitable amounts of silver for the photographic materials of the present invention are $1\times10^{-3}$ to $3\times10^{-1}$ mol/m$^2$. With color light-sensitive materials containing a reduced amount of silver halide, suitable color images can be obtained by, for example, halogenation-bleaching silver deposits formed by color development and again conducting color development to increase the amount of dye produced (for example, U.S. Pat. Nos. 2,623,822, 2,814,565, etc.), or by employing a development processing utilizing color intensification using peroxides or cobalt complex salts to increase the amount of dye produced (for example, West German Patent Application (OLS) No. 2,357,694, U.S. Pat. Nos. 3,674,490, 3,761,265, West German Patent Application (OLS) Nos. 2,044,833, 2,056,359, 2,056,360, 2,226,770, Japanese Patent Application (OPI) Nos. 9728/73 and 9729/73, etc.)

The 2-equivalent magenta coupler of this invention can be used together with other magenta couplers, as described, for instance, in U.S. Pat. Nos. 2,439,098, 2,369,489, 2,600,788, 3,558,319, 2,311,081, 3,419,391, 3,214,437, 3,006,759, 2,725,292, 3,408,194, 2,908,573, 3,519,429, 3,615,506, 3,432,521, 3,152,896, 3,062,653, 3,582,322, 2,801,171, 3,311,476, 3,907,571, 3,935,015, 3,960,571, 4,163,670, British Patents 956,261, 1,420,637, French Patent 7,417,395, Japanese Patent Publication Nos. 2016/69 and 19032/71, with the magenta-colored couplers, as described in U.S. Pat. Nos. 2,983,608, 2,455,170, 2,725,292, 3,005,712, 3,519,429, and 2,688,539, British Pat. Nos. 800,262 and 1,044,778, and Belgian Pat. No. 676,691, with the so-called development inhibitor releasing type couplers capable of imagewise releasing development inhibiting compounds at development, such as, for instance, the monothio type couplers as described in U.S. Pat. Nos. 3,227,550 and 3,227,554 and British Pat. No. 953,454, the o-aminophenylazo type couplers as described in U. S. Pat. No. 3,148,062, and the couplers as described in Japanese Patent Publication No. 8750/72 and German Patent Application (OLS) No. 2,163,811, and also with the hydroquinone releasing development inhibiting compounds as described in U.S. Pat. No. 3,297,445 and British Pat. No. 1,058,606.

One or more of the above-described couplers and the like can be employed in the same layer to achieve the properties required for a particular light-sensitive material and, of course, the same compound can be incorporated in two or more different layers. In general, the couplers are coated at a coverage of about $1\times10^{-4}$ to $5\times10^{-3}$ mol/m$^2$, preferably $3\times10^{-4}$ to $2\times10^{-3}$ mol/m$^2$.

The light-sensitive material of the present invention advantageously contains a p-substituted phenol derivative in an emulsion layer or an adjacent layer for the purpose of improving the light fastness of the magenta dye formed or of preventing yellowing or print-out of a coupler remaining in the unexposed areas, color fogging, or the like. Particularly effective p-substituted phenol derivatives are the hydroquinone derivatives described in U.S. Pat. Nos. 2,360,290, 2,418,613, 2,675,314, 2,701,197, 2,704,713, 2,710,801, 2,728,659, 2,732,300, 2,735,765, 2,816,038; the gallic acid derivatives as described in U.S. Pat. Nos. 3,457,079, 3,069,262 and Japanese Patent Publication No. 13496/68; the p-alkoxyphenol derivatives as described in U.S. Pat. No. 2,735,765 and Japanese Patent Application (OPI) No. 4738/72; and p-hydroxyphenol derivatives as described in U.S. Pat. Nos. 3,342,300, 3,573,050, 3,574,627 and Japanese Patent Publication No. 20977/74.

The silver halide emulsion which can be used in this invention can be suitably selected from various kinds of photographic emulsions depending on the end-use purposes of the photographic materials. Suitable silver halides which can be used in this invention include silver chloride, silver chlorobromide, silver bromide, silver iodobromide, and silver chloroiodobromide. Also, suitable binders for the silver halide emulsions which can be used in this invention are gelatin, gelatin derivatives (e.g., the acrylated gelatin as described in U.S. Pat. No. 3,118,766 and the graft gelatin having as the branch component a vinyl monomer such as acrylic acid as described in U.S. Pat. No. 2,831,767), casein, albumin, agar agar, sodium alginate, starch, cellulose derivatives (e.g., carboxymethyl cellulose and hydroxyethyl cellulose), vinyl alcohol, vinylpyrrolidone, polyacrylamide, and the like.

The silver halide emulsions used in this invention can be prepared by a single jet method, a double jet method, a control double jet method, and further the halogen conversion method, as described in British Pat. No. 635,841 and U.S. Pat. No. 3,622,318.

The silver halide emulsion used in this invention can be sensitized by the natural sensitizers present in gelatin, by a sulfur sensitizer, by a reductive sensitizer, and by a noble metal salt using conventional techniques.

The silver halide emulsion can contain an anti-fogging agent or a stabilizer such as 1-phenyl-5-mercaptotetrazole, 5-methyl-7-hydroxy-1,3,4,7a-tetraazaindene, etc. Also, the silver halide emulsion can contain a sensitizing dye such as a cyanine dye, a merocyanine dye, etc. The silver halide emulsion can contain a coating aid such as saponin, polyethyleneglycol monolauryl ether, etc. Furthermore, the silver halide emulsion can contain a thickener such as polystyrenesulfonic acid, etc., an ultraviolet absorber such as 2-(2-hydroxy-3,5-di-sec-butylphenyl)-5-methoxybenzotriazole, 4-methoxy-α-cyanocinnamic acid-n-dodecyl ester, etc., an antioxidant or a reducing agent such as sodium bisulfite, ascorbic acid, aminophenols, pyrogallols, gallic acids, catechols, resorcinols, and dihydroxynaphthalenes, and an irradiation preventing dyes such as an oxonol dye and a styryl dye, and other conventional photographic additives, if desired.

A photographic light-sensitive material according to the present invention comprises a support having thereon a silver halide emulsion layer containing a 2-equivalent magenta coupler in accordance with the present invention. One embodiment of a photograpic light-sensitive material according to this invention comprises a multilayered, multicolored photographic light-sensitive silver halide emulsion layer containing a yellow coupler (that is, a coupler that forms a yellow dye), a green-sensitive silver halide emulsion layer containing a magenta coupler in accordance with the present invention, and a red-sensitive silver halide emulsion layer containing a cyan coupler (that is, a coupler that forms a cyan dye). Known blue-sensitive silver halide emulsions and the red-sensitive silver halide emulsions can be appropriately used. Open-chain type ketomethylene compounds represented by benzoylacetanilides and pivaloylacetanilides can advantageously be used as yellow color-forming couplers. Phenolic or naptholic compounds can advantageously be used as cyan color-forming couplers. Such color-forming couplers can contain a coupling-off group on the carbon atom of the coupling position, and are desirably non-diffusible.

The photographic light-sensitive material of the present invention can have, in addition to the aforesaid silver halide emulsion layers, light-sensitive auxiliary layers such as a protective layer, a filter layer, intermediate layers, an antihalation layer, and a backing layer.

The hydrophilic polymer material, particularly gelatin constituting the layers of the photographic light-sensitive material of the present invention can be hardened by various cross-linking agents. For example, although an inorganic compound such as a chromium salt and a zirconium salt, and an aldehyde type cross-linking agent such as mucochloric acid, 2-phenoxy-3-chloromalealdehydic acid, etc., as described in Japanese Patent Publication No. 1872/71 can be used, a non-aldehyde type cross-linking agent, for example, a polyepoxy compound as described in Japanese Patent Publication No. 7133/59, a poly(1-aziridinyl) compound as described in Japanese Patent Publication No. 8790/62, an active halogen compound as described in U.S. Pat. Nos. 3,362,827 and 3,325,287, etc., are particularly useful.

In the photographic light-sensitive materials of the present invention, any materials usually used as supports for photographic light-sensitive materials can be suitably used. For instance, preferred examples of such supports are cellulose ester films such as cellulose nitrate films, cellulose acetate films, etc., polyester films such as polyethylene terephthalate films, etc., polyvinyl chloride films, polyvinyl acetal films, polystyrene films, polycarbonate films, polyamide films such as nylon films, baryta-coated papers, α-olefin polymercoated papers, and so forth.

The photographic light-sensitive material of the present invention can be suitably used for various purposes such as color positive films, color negative films, color reversal films, color photographic printing papers, and so forth.

The color photographic light-sensitive material of the present invention provides magenta color images having excellent spectral properties and image fastness when imagewise exposed in a conventional manner and processed using conventional color processing steps. The main color processing steps are color development, bleach, and fix and if desired a wash step can be inserted between each of the steps.

A useful color developer which can be used for developing the color photographic material of this invention is an alkaline aqueous solution containing a color developing agent, and having a pH of from about 9.5 to 12.2. Examples of color developing agents which can be used in the color developer include conventional primary aromatic amine color developing agents such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-diethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline), and p-aminophenols (e.g., 4-aminophenol, 2,6-dichloro-4-aminophenol, 2-bromo-4-aminophenol, and 2,6-diiodo-4-aminophenol).

The color developer can contain further conventional additives such as, for instance, an alkali metal sulfite, an alkali metal carbonate, an alkali metal bisulfite, a bromide, an iodide, an alkaline buffer, etc. Furthermore, if desired, the color developer can contain a dye forming coupler, a competitive coupler, an antifoggant, a hardening agent, an antioxidant, a thickener, and so forth.

Some of the advantages of the present invention are as follows.

(1) Since the amount of silver necessary for obtaining the same magenta color image density can be reduced, the thickness of the light-sensitive layer containing the coupler can be reduced, thus improving the sharpness of the images obtained.

(2) The heat fastness of the magenta color images produced using the coupler of the present invention is improved.

(3) The production cost can be reduced through the reduction in the amount of silver halide necessary.

(4) Magenta couplers stable to chemicals such as formaldehyde or acetone can be obtained.

(5) Couplers having a high developing activity can be obtained.

(6) Color images with less fog and stain and with excellent other photographic properties can be obtained.

(7) Silver halide color photographic light-sensitive materials having excellent storage stability can be obtained using the coupler of the present invention.
(8) The conversion of the coupler to the dye is improved using the coupler of the present invention.
(9) Silver halide color photographic light-sensitive materials having high sensitivity can be obtained using the coupler of the present invention.

The light-sensitive materials of the present invention having the above-described advantages are extremely useful in the field of color photography.

The present invention will now be illustrated in more detail by the following non-limiting examples of preferred embodiments of the present invention.

EXAMPLE 1

A solution, prepared by heating at 60° C. and dissolving a mixture comprising 23.0 g of Coupler (1) in accordance with the present invention, 20 ml of dioctyl butyl phosphate and 60 ml of ethyl acetate, was added to 250 ml of a 60° C. aqueous solution containing 2.5 g of gelatin and 0.75 g of sodium dodecylbenzenesulfonate. The resulting solution was mechanically vigorously stirred using a homogenizer to obtain a coupler emulsion dispersion. This emulsion dispersion was mixed with 200 g of a photographic emulsion containing $11.2 \times 10^{-2}$ mol of silver chlorobromide (silver bromide: 45 mol %, silver chloride: 55 mol %) and 20 g of gelatin. Then, 10 ml of a 3% acetone solution of triethylenephosphoramide was added thereto as a hardener and, after adjusting the final pH to 6.5, the solution was coated on a cellulose triacetate film support in a dry thickness of 4.5μ (Film A). This film contained $1.54 \times 10^{-3}$ mol/m² of Coupler (1) and $6.2 \times 10^{-3}$ mol/m² of silver chlorobromide.

25.2 g of Coupler (2) in accordance with the present invention and, as comparision couplers, 19.6 g of 1-(2,4,6-trichlorophenyl)-3-{3-[2-(2,4-di-tert-amylphenoxy)-butyramido]benzamido}-5-oxo-2-pyrazoline (Coupler L), 23.4 g of 1-(2,4,6-trichlorophenyl)-3-{3-[2-(3-pentadecylphenoxy)butyramido]benzamido}-4-(1-imidazolyl)-5-oxo-2-pyrazoline (Coupler M), 21.4 g of 1-(2,4,6-trichlorophenyl)-3-[2-(2,4-di-tert-amylphenoxy)butyramido]-4-(1-imidazolyl)-5-oxo-2-pyrazoline (Coupler N) and 25.1 g of (2,6-dichloro-4-methoxyphenyl)-3-}3-[2-(3-tert-butyl-4-hydroxyphenoxy)tetradecanamido]benzamido}-4-(2-phenyl-1-imidazolyl)-5-oxo-2-pyrazoline (Coupler O) were dispersed respectively in place of the above-described Coupler (1) in the same manner as described above, mixed with 200 g of a silver halide emulsion having the same composition as above with respect to Coupler (2), Coupler (M), Coupler (N), and Coupler (O) and with 400 g of a silver halide emulsion having the same composition as above with respect to Coupler (L) respectively, and coated on a film in a dry thickness of 4.6μ, 5.3μ, 4.5μ, 4.6μ and 4.6μ respectively (Films B, C, D, E and F). The coated amounts of coupler and silver chlorobromide emulsion on the films were shown in Table 1 below.

These films were subjected to stepwise exposure and the following development processing steps.

| Color Development Processing: | | | |
|---|---|---|---|
| 1. | Color Development | 21° C. | 12 min |
| 2. | Washing | " | 30 sec |
| 3. | First Fixing | " | 4 min |
| 4. | Washing | " | 4 min |
| 5. | Bleaching | " | 8 min |
| 6. | Washing | " | 4 min |
| 7. | Second Fixing | " | 4 min |
| 8. | Washing | " | 6 min |

The processing solutions had the following compositions.

| Color Development Solution | |
|---|---|
| Sodium Hexametaphosphate | 2 g |
| Sodium Sulfite (anhydrous) | 2 g |
| Sodium Carbonate (monohydrate) | 27.5 g |
| Potassium Bromide | 0.5 g |
| Hydroxylamine Sulfate | 2.5 g |
| N-Ethyl-N-(β-methanesulfonamidoethyl)-3-methyl-4-aminoaniline Sesquisulfate | 2.5 g |
| Water to make | 1 l |
| | pH = 10.7 |
| Fixing Solution | |
| Sodium Thiosulfate (hexahydrate) | 80 g |
| Sodium Sulfite (anhydrous) | 5 g |
| Borax | 6 g |
| Glacial Acetic Acid | 4 ml |
| Potassium Alum | 7 g |
| Water to make | 1 l |
| | pH = 4.5 |
| Bleaching Bath | |
| Potassium Ferricyanide | 100 g |
| Potassium Bromide | 5 g |
| Boric Acid | 10 g |
| Borax | 5 g |
| Water to make | 1 l |
| | pH = 7.2 |

After processing, the optical density of these film samples was measured using green light. As a result, the photographic properties as shown in Table 1 were obtained.

TABLE 1

| | | Photographic Properties | | | | | | | |
|---|---|---|---|---|---|---|---|---|---|
| | | Coated Amount (mol/m²) | | Ag/Coupler | Film | | | Relative | Maximum Color |
| Film | Coupler | Coupler (M) | Ag × (M) | (molar ratio) | Thickness | Fog | Gamma | Sensitivity | Density |
| A | (1) | $1.54 \times 10^{-3}$ | $6.2 \times 10^{-3}$ | 4 | 4.5 | 0.03 | 4.2 | 100 | 3.40 |
| B | (2) | $1.55 \times 10^{-3}$ | $6.3 \times 10^{-3}$ | 4 | 4.6 | 0.02 | 4.0 | 97 | 3.37 |
| C | (L) | $1.55 \times 10^{-3}$ | $12.5 \times 10^{-3}$ | 8 | 5.3 | 0.02 | 1.9 | 63 | 2.05 |
| D | (M) | $1.54 \times 10^{-3}$ | $6.3 \times 10^{-3}$ | 4 | 4.5 | 0.02 | 2.7 | 75 | 2.80 |
| E | (N) | $1.56 \times 10^{-3}$ | $6.3 \times 10^{-3}$ | 4 | 4.6 | 0.03 | 2.2 | 72 | 2.43 |
| F | (O) | $1.55 \times 10^{-3}$ | $6.4 \times 10^{-3}$ | 4 | 4.6 | 0.02 | 2.8 | 76 | 2.83 |

The results in Table 1 show that the coupler according to the present invention provided higher sensitivity, higher gradation (gamma) and higher maximum color density in comparison with the 4-equivalent coupler even when the ratio of silver halide/coupler was reduced to about ½. Also, in comparison with Films D, E and F, the coupler according to the present invention indicated superior color forming properties to the 2-equivalent Couplers M, N and O having an imidazolyl group as the coupling-off group (M, N and O are couplers of the type described in German Pat. No. 2,536,191).

EXAMPLE 2

The following processings were conducted after exposure of Films A, B, C, D, E and F described in Example 1.

| Color Development Processing | | | |
|---|---|---|---|
| 1. | Color Development | 30° C. | 4 min |
| 2. | Bleach-Fixing | " | 2 min |
| 3. | Washing | " | 2 min |
| 4. | Stabilizing Bath | " | 2 min |

The photographic properties of the thus obtained films are shown in Table 2 below.

Furthermore, as aqueous stabilizing baths a formaldehyde free Stabilizing Bath (a) and Stabilizing Bath (b) containing 1% of a 40% by weight aqueous solution of formaldehyde were used. With the two films having been processed, the reduction ratio of the density based on the initial density, after leaving the films at 80° C. for 2 weeks was determined and the results are tabulated in Table 3 below. Also, the occurrence of stain under the same condition as above are tabulated in Table 4 below.

| Color Developer | |
|---|---|
| Sodium Metaborate | 25 g |
| Sodium Sulfite | 2 g |
| Hydroxylamine (sulfate) | 2 g |
| Potassium Bromide | 0.5 g |
| 6-Nitrobenzimidazole (nitrate) | 0.02 g |
| Sodium Hydroxide | 4 g |
| Diethylene Glycol | 20 ml |
| 4-(N-Ethyl-N- -methanesulfonamido-ethyl)amino-2-methylaniline Sesquisulfate | 8 g |
| Water to make | 1 l |
| | pH = 10.2 |
| Bleach-Fixing Solution | |
| Ferric Salt of Ethylenediaminetetra acetic Acid | 45 g |
| Ammonium Thiocyanate | 10 g |
| Sodium Sulfite | 10 g |
| Ammonium Thiosulfate (60% aq. soln.) | 100 ml |
| Sodium Ethylenediaminetetraacetate | 5 g |
| Water to make | 1 l |
| | pH = 6.9 |
| Stabilizing Bath (a) | |
| Tartaric Acid | 10 g |
| Zinc Sulfate | 10 g |
| Sodium Metaborate | 20 g |
| Water to make | 1 l |
| Stabilizing Bath (b) | |
| Tartaric Acid | 10 g |
| Zinc Sulfate | 10 g |
| Sodium Metaborate | 20 g |
| Formalin (40%) | 10 ml |
| Water to make | 1 l |

TABLE 2

| Photographic Properties (using Stabilizing Bath (a)) | | | |
|---|---|---|---|
| Film | Coupler | Fog | Gamma | Maximum Color Density |
| A | (1) | 0.03 | 4.1 | 3.38 |
| B | (2) | 0.02 | 4.0 | 3.36 |
| C | (L) | 0.02 | 1.73 | 2.01 |
| D | (M) | 0.02 | 2.65 | 2.72 |
| E | (N) | 0.02 | 2.18 | 2.36 |

TABLE 2-continued

| Photographic Properties (using Stabilizing Bath (a)) | | | |
|---|---|---|---|
| Film | Coupler | Fog | Gamma | Maximum Color Density |
| F | (O) | 0.03 | 2.79 | 2.77 |

TABLE 3

Fastness of Color Images (after storage for 2 weeks at 80° C.)

| Film | Stabilizing Bath | Reduction Ratio (%) in Color Image Density Initial Density | | |
|---|---|---|---|---|
| | | 0.5 | 1.0 | 2.0 |
| A | a | 5 | 3 | 2 |
| | b | 5 | 2 | 2 |
| B | a | 6 | 3 | 2 |
| | b | 5 | 2 | 2 |
| C | a | 65 | 49 | 18 |
| | b | 10 | 9 | 6 |

TABLE 4

Occurrence of Stain in Unexposed Areas (using Stabilizing Bath (a) and after storate for 2 weeks at 80° C.)

| Film | Initial Density (B) | Density (B) after Storage for 2 weeks at 80° C. |
|---|---|---|
| A | 0.03 | 0.03 |
| B | 0.02 | 0.02 |
| D | 0.02 | 0.07 |
| E | 0.02 | 0.09 |
| F | 0.03 | 0.08 |

The results in Table 2 show that, even when a strong oxidizing agent used in the development processing of Example 1 is not used, sufficient color forming properties can be obtained using the film containing the couplers according to the present invention. The results in Table 3 show that Films A and B provide sufficient heat fastness even without a stabilization using formaldehyde in a conventional manner. The results in Table 4 show that the occurrence of stain in Films A and B is extremely small in comparision with Films D, E and F each containing known 2-equivalent magenta couplers, which proves the stability of the couplers according to the present invention.

EXAMPLE 3

A solution obtained by dissolving 4.5 g of Coupler (19) of the present invention, 6.0 ml of tricresyl phosphate and 12 ml of ethyl acetate with heating at 60° C. was added to 40 ml of an aqueous solution containing 4 g of gelatin, 0.10 g of sodium dodecylbenzenesulfonate at 60° C. The solution mixture was stirred with a homogenizer to prepare a coupler dispersion. The coupler dispersion was mixed with 60 g of a green-sensitive photographic emulsion containing $4.70 \times 10^{-2}$ mol of silver chlorobromide (50 mol % silver chloride) and 9 g of gelatin, and 5 ml of a 3% acetone solution of triethylenephosphoramide was further added thereto as a hardening agent. After adjusting the pH to 7.0, the dispersion was coated onto a paper sheet having polyethylene coated thereon to obtain a dry thickness of 2.8 microns (hereafter all thicknesses given are dry thicknesses). Gelatin was coated thereon (using a 2% gelatin aqueous solution) in a thickness of 1 micron to prepare a color printer paper (Sample G).

Additional color print papers were prepared by dispersing in the same manner described above, except that equimolar amounts of Couplers (21) and (23) according to the present invention were employed in lieu of Coupler (19), and equimolar amounts of 1-(2,4,6-trichlorophenyl)-3-(2-chloro-5-tetradecanamidoanilino)-5-oxo-2-pyrazoline (Coupler P), 3-{5-[2(2,4-di-tert-amylphenoxy)butyramido]-2-chloroanilino}-1-(2,4,6-trichlorophenyl-5-oxo-2-pyrazoline (Coupler Q) and 3-(2-chloro-5-tetradecyloxycarbonylaminoanilino)-1-(2,4,6-trichlorophenyl)-4-imidazolyl-5-oxo-2-pyrazoline (Coupler R) were employed as magneta color image-forming couplers for comparison, respectively, mixing with 60 g of a silver halide emulsion having the same composition as above with respect to Coupler (21), Coupler (23) and Coupler (R) and with 100 g of a silver halide emulsion having the same composition as above with respect to Coupler (P) and Coupler (Q) respectively, and coating on a film. Samples using Coupler (21), Coupler (23), Coupler (P), Coupler (Q) and Coupler (R) are designated Color Print Papers H, I, J, K and S, respectively.

These samples were exposed to green light using a step wedge and processed using the following development processing steps.

| Processing Step | Temperature | Time |
| --- | --- | --- |
| 1. Color Development | 30° C. | 4 min |
| 2. Bleach-Fixing | " | 2 min |
| 3. Water Washing | " | 2 min |
| 4. Stabilizing | " | 2 min |

The processing solutions used had the following compositions:

| Composition of Color Developer | |
| --- | --- |
| Sodium Metaborate | 25 g |
| Sodium Sulfite | 2 g |
| Hydroxylamine (Sulfate) | 2 g |
| Potassium Bromide | 0.5 g |
| 6-Nitrobenzimidazole (nitrate) | 0.02 g |
| Sodium Hydroxide | 4 g |
| Benzyl Alcohol | 15.8 ml |
| Diethylene Glycol | 20 ml |
| 4-(N-Ethyl-N- -methanesulfonamidoethyl)- amino-2-methylaniline Sesquisulfate | 8 g |
| Water to make | 1 l |
| Composition of Bleach-Fixing Solution | |
| Ferric Salt of Ethylenediaminetetraacetate | 45 g |
| Ammonium Thiocyanate | 10 g |
| Sodium Sulfite | 10 g |
| Ammonium Thiosulfate (60% aq. soln.) | 100 ml |
| Tetrasodium ethylenediaminetetraacetate | 5 g |
| Water to make | 1 l |
| Composition of Stabilizing Bath (a) | |
| Tartaric Acid | 10 g |
| Zinc Sulfate | 10 g |
| Sodium Metaborate | 20 g |
| Water to make | 1 l |

With respect to the samples obtained, the yellow stain density in the unexposed area was determined by measuring the reflection density thereof with a densitometer equipped with a blue filter. Thereafter, these samples were stored for 2 weeks under a fluorescent light (about 28,000 lux) and the rate of increase in the yellow stain density was measured. The results obtained are shown in Table 5 below.

TABLE 5

Occurrence of Stain in Unexposed Areas
(after storage under fluorescent lamp for 2 weeks)

| Color Paper Sample No. | Coupler Used | Yellow Stain Density in Unexposed Areas | |
| --- | --- | --- | --- |
| | | Initial Density | After Irradiation |
| G | (19) | 0.02 | 0.03 |
| H | (21) | 0.02 | 0.03 |
| I | (23) | 0.02 | 0.03 |
| J | (P) | 0.02 | 0.06 |
| K | (Q) | 0.02 | 0.08 |
| S | (R) | 0.03 | 0.15 |

It is clear from the results shown in Table 5 above that the samples using the magenta couplers of the present invention had a low yellow stain density in the unexposed areas initially, and show much less increase in yellow stain density upon irradiation with light then the comparative samples.

While the invention has been described in detail and with reference to specific embodiments thereof, it will be apparent to one skilled in the art that various changes and modifications can be made therein without departing from the spirit and scope thereof.

What is claimed is:

1. A process for forming a color photographic image comprising processing a silver halide color photographic light-sensitive material in the presence of a 5-pyrazolone magenta coupler represented by the formula (I):

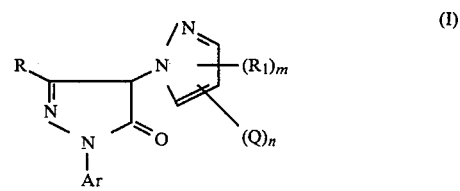

wherein R represents an acylamino group, an anilino group or a ureido group; $R_1$ represents a nitro group, a nitroso group, an amino group, an acylamino group represented by the formula (II)

a sulfonamido group represented by the formula (III)

a urethane group, a diacylamino group represented by the formula (V)

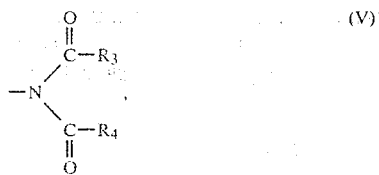

or a ureido group, wherein R₂ in the formula (II) and (III) represents a hydrogen atom, a straight chain or branched chain alkyl group, an alkenyl group, a cycloalkyl group, an aralkyl group, an aryl group or a heterocyclic group, and R₃ in the formula (II) and (III) represents a straight chain or branched chain alkyl group, an alkenyl group, a cycloalkyl group, an aralkyl group, an aryl group or a heterocyclic group; or R₂ and R₃ in the formula (II) and (III) together form a 5-membered, 6-membered, or 7-membered nitrogen-containing heterocyclic ring, and R₃ and R₄ in the formula (V) each represents a straight chain or branched chain alkyl group, an alkenyl group, a cycloalkyl group, an aralkyl group, an aryl group or a heterocyclic group, or R₃ and R₄ in the formula (V) together form a 5-membered, 6-membered, or 7-membered nitrogen-containing heterocyclic ring; Q represents a hydrogen atom, a halogen atom, a substituted or unsubstituted alkyl group, an alkenyl group, a cycloalkyl group, an aralkyl group, an alkoxy group, an aryloxy group, a carboxy group, a substituted or unsubstituted aryl group, a substituted or unsubstituted heterocyclic group, a thiourethane group, a thioureido group, an acylhydrazino group, an alkylamino group, a dialkylamino group, an anilino group, an alkylthio group, a mercapto group, an arylthio group, an alkylsulfinyl group, an alkylsulfonyl group, an arylsulfinyl group, an arylsulfonyl group, a sulfamoyl group, a sulfo group, a thiocyano group, a hydroxy group, an aminocarbonyloxy group, an acyloxy group, a sulfonyloxy group, an alkylcarbonyl group, an arylcarbonyl group, an alkoxycarbonyl group, an aryloxycarbonyl group, a carbamoyl group, an aralkyloxycarbonyl group, or a cyano group; Ar represents a phenyl group which may be substituted with one or more halogen atoms, alkyl groups, alkoxy groups and cyano groups; m represents an integer; n represents 0, 1 or 2; and m and n must satisfy the following relation $1 \leq m+n \leq 3$.

2. A process as in claim 1, wherein R represents an acylamino group selected from the group consisting of an acetamido group, a benzamido group, a 3-[α-(2,4-di-tert-amylphenoxy)butyramido]benzamido group, a 3-[α-(2,4-di-tert-amylphenoxy)-acetamido]benzamido group, a 3-[α-(3-pentadecylphenoxy)-butyramido]benzamido group, an α-(2,4-di-tert-amylphenoxy)-butyramido group, and on α-(3-pentadecylphenoxy)-butyramido group.

3. A process as in claim 1, wherein R represents an anilino group selected from the group consisting of an unsubstituted anilino group, a 2-chloroanilino group, a 2,4-dichloroanilino group, a 2-chloro-5-tetradecanamidoanilino group, a 2-chloro-5-(2-octadecenylsuccinimido)anilino group, a 2-chloro-5-[α-(3-tert-butyl-4-hydroxy)tetradecanamido]anilino group, a 2-chloro-5-tetradecyloxycarbonylanilino group, a 2-chloro-5-(N-tetradecylsulfamoyl)anilino group, and a 2,4-dichloro-5-tetradecyloxyanilino group.

4. A process as in claim 1, wherein R represents a ureido group selected from the group consisting of 3-[(2,4-di-tert-amylphenoxy)-acetamido]phenylureido group, a phenylureido group, a methylureido group, an octadecylureido group, and a 3-tetradecanamidophenylureido group.

5. A process as in claim 1, wherein R₁ represents a urethane group represented by the formula (IV)

wherein R₂ in the formula (IV) represents a hydrogen atom, a straight chain or branched chain alkyl group, an alkenyl group, a cycloalkyl group, an aralkyl group, an aryl group or a heterocyclic group; and R₃ in the formula (IV) represents a straight chain or branched chain alkyl group, an alkenyl group, a cycloalkyl group, an aralkyl group, an aryl group or a heterocyclic group; or R₂ and R₃ in the formula (IV) together form a 5-membered, 6-membered, or 7-membered nitrogen-containing heterocyclic ring.

6. A process as in claim 1, wherein R₁ represents a ureido group represented by the formula (VI)

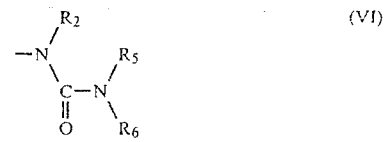

wherein R₂, R₅ and R₆ in the formula (VI) each represents a hydrogen atom, a straight chain or branched chain alkyl group, an alkenyl group, a cycloalkyl group, an aralkyl group, an aryl group or a heterocyclic group; or R₂ and R₅ in the formula (VI) together, or R₅ and R₆ in the formula (VI) together form a 5-membered, 6-membered, or 7-membered nitrogen-containing heterocyclic ring.

7. A process as in claim 5 or 6, wherein said alkyl groups, alkenyl groups, cycloalkyl groups, aralkyl groups, aryl groups and hetrocyclic groups may have one or more substituents selected from the group consisting of a halogen atom, a nitro group, a cyano group, a thiocyano group, an aryl group, an alkoxy group, an aryloxy group, a carboxy group, a sulfoxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, and a mercapto group, and said aryl groups and heterocyclic groups may be further substituted by an alkyl group, an alkenyl group, a cycloalkyl group, and an aralykl group.

8. A process as in claim 1, wherein said 5-pyrazolone magenta coupler is present in a silver halide light-sensitive color photographic material.

9. A process as in claim 1 comprising bleachfixing said color photographic material after color development.

10. A color photographic light-sensitive material comprising a support having thereon at least one silver-halide emulsion layer, and at least one layer containing a 5-pyrazolone magenta coupler represented by the formula (I)

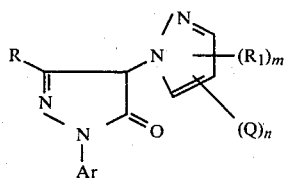

wherein R represents an acylamino group, an anilino group or a ureido group; $R_1$ represents a nitro group, a nitroso group, an amino group, an acylamino group represented by the formula (II)

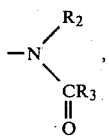

a sulfonamido group represented by the formula (III)

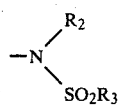

a urethane group, a diacylamino group represented by the formula (V)

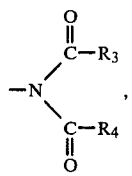

or a ureido group, wherein $R_2$ in the formula (II) and (III) represents a hydrogen atom, a straight chain or branched chain alkyl group, an alkenyl group, a cycloalkyl group, an aralkyl group, an aryl group or a heterocyclic group, and $R_3$ in the formula (II) and (III) represents a straight chain or branched chain alkyl group, an alkenyl group, a cycloalkyl group, an aralykyl group, an aryl group or a heterocyclic group; or $R_2$ and $R_3$ in the formula (II) and (III) together form a 5-membered, 6-membered, or 7-membered nitrogen-containing heterocyclic ring, and $R_3$ and $R_4$ in the formula (V) each represents a straight chain or branched chain alkyl group, an alkenyl group, a cycloalkyl group, and aralkyl group, an aryl group or a heterocyclic group, or $R_3$ and $R_4$ in the formula (V) together form a 5-membered, 6-membered, or 7-membered nitrogen-containing heterocyclic ring; Q represents a hydrogen atom, a halogen atom, a substituted or unsubstituted alkyl group, an alkenyl group, a cycloalkyl group, an aralkyl group, an alkoxy group, an aryloxy group, a carboxy group, a substituted or unsubstituted aryl group, a substituted or unsubstituted heterocyclic group, a thiourethane group, a thioureido group, an acylhydrazino group, an alkylamino group, a dialkylamino group, an anilino group, an alkylthio group, a mercapto group, an arylthio group, an alkylsulfinyl group, an alkylsulfonyl group, an arylsulfinyl group, an arylsulfonyl group, a sulfamoyl group, a sulfo group, a thiocyano group, a hydroxy group, an aminocarbonyloxy group, an acyloxy group, a sulfonyloxy group, an alkylcarbonyl group, an arylcarbonyl group, an alkoxycarbonyl group, an aryloxycarbonyl group, a carbamoyl group, an aralkyloxycarbonyl group, or a cyano group; Ar represents a phenyl group which may be substituted with one or more halogen atoms, alkyl groups, alkoxy groups and cyano groups; m represents an integer; n represents 0, 1 or 2; and m and n must satisfy the following relation $1 \leq m+n \leq 3$.

11. A color photographic light-sensitive material as in claim 10, wherein R represents an acylamino group selected from the group consisting of an acetamido group, a 3-[-(2,4-di-tert-amylphenoxy)butyramido]benzamido group, a 3-[α(2,4-di-tert-amylphenoxy)acetamido]benzamido group, a 3-[α-(3-pentadecylphenoxy)butyramido]benzamido group, an α-(2,4-di-tert-amylphenoxy)butyramido group, and a α-(3-pentadecylphenoxy)butyramido group.

12. A color photographic light-sensitive material as in claim 10, wherein R represents an anilino group selected from the group consisting of an unsubstituted anilino group, a 2-chloroanilino group, a 2,4-dichloroanilino group, a 2-chloro-5-tetradecanamidoanilino group, a 2-chloro-5-(2-octadecenylsuccinimido)anilino group, a 2-chloro-5-[α-(3-tert-butyl-4-hydroxy)tetradecanamido]anilino group, a 2-chloro-5-tetradecyloxycarbonylanilino group, a 2-chloro-5-(N-tetradecylsulfamoyl)anilino group, and a 2,4-dichloro-5-tetradecyloxyanilino group.

13. A color photographic light-sensitive material as in claim 10, wherein R represents a ureido group selected from the group consisting of a 3-[(2,4-di-tert-amylphenoxy)acetamido]-phenylureido group, a phenylureido group, a methylureido group, an octadecylureido group, and a 3-tetradecanamidophenylureido group.

14. A color photographic light-sensitive material as in claim 10, wherein $R_1$ represents a urethane group represented by the formula (IV)

wherein $R_2$ in the formula (IV) represents a hydrogen atom, a straight chain or branched chain alkyl group, an alkenyl group, a cycloalkyl group, an aralkyl group, an aryl group or a heterocyclic group; and $R_3$ represents a straight chain or branched chain alkyl group, an alkenyl group, a cycloalkyl group, an aralkyl group, an aryl group or a heterocyclic group; or $R_2$ and $R_3$ in the formula (IV) together form a 5-membered, 6-membered, or 7-membered nitrogen-containing heterocyclic ring.

15. A color photographic light-sensitive material as in claim 10, wherein $R_1$ represents a ureido group represented by the formula (VI)

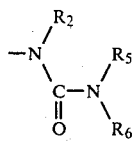 (VI)

wherein $R_2$, $R_5$ and $R_6$ each represents hydrogen, a straight chain or branched chain alkyl group, an alkenyl group, a cycloalkyl group, an aralkyl group, an aryl group or a heterocyclic group; or $R_2$ and $R_5$ together, or $R_5$ and $R_6$ together form a 5-membered, 6-membered, or 7-membered nitrogen containing heterocyclic ring.

16. A color photographic light-sensitive material as in claim 14 or 15, wherein said alkyl groups, alkenyl groups, cycloalkyl groups, aralkyl groups, aryl groups and heterocyclic groups may have one or more substituents selected from the group consisting of a halogen atom, a nitro group, a cyano group, a thiocyano group, an aryl group, an alkoxy group, an aryloxy group, a carboxy group, a sulfoxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group, and a mercapto group, and said aryl groups and heterocyclic groups may be further substituted by an alkyl group, an alkenyl group, a cycloalkyl group, and an aralkyl group.

17. A color photographic light-sensitive material as in claim 10, wherein said 5-pyrazolone magenta coupler is present in a silver halide emulsion layer.

18. A color photographic light-sensitive material as in claim 17, wherein said emulsion layer is a green-sensitive emulsion layer.

19. A color photographic light-sensitive material as in claim 18 comprising a support having therein at least one blue-sensitive silver halide emulsion layer containing a yellow coupler, said green-sensitve silver halide emulsion layer containing said magenta coupler, and a red-sensitive silver halide emulsion layer containing a cyan coupler.

20. A color photographic light-sensitive material as in claim 19, wherein said couplers are non-diffusible.

21. A color photographic light-sensitive material as in claim 10, wherein said magenta coupler includes a group having a hydrophobic residue containing from 8 to 32 carbon atoms.

22. A color photographic light-sensitive material as in claim 17, wherein said magenta coupler is present as a dispersion thereof.

23. A color photographic light-sensitive material as in claim 10, 11, 12, 13, 14, 15, 17, 18, 19, 20, 21, or 22, wherein the concentration of the magenta coupler is from $2 \times 10^{-3}$ to $5 \times 10^{-1}$ moles per mole of silver.

24. A color photographic light-sensitive material as in claim 16, wherein the concentration of the magenta coupler is from $2 \times 10^{-3}$ to $5 \times 10^{-1}$ moles per mole of silver.

25. A color photographic light-sensitive material as in claims 10, 11, 12, 13, 14, 15, 17, 18, 19, 20, 21, or 22, wherein the concentration of the magenta coupler is from $1 \times 10^{-2}$ to $5 \times 10^{-1}$ moles per mole of silver.

26. A color photographic light-sensitive material as in claim 16, wherein the concentration of the magenta coupler is from $1 \times 10^{-2}$ to $5 \times 10^{-1}$ moles per mole of silver.

* * * * *